United States Patent [19]

Frost

[11] Patent Number: 4,606,350
[45] Date of Patent: Aug. 19, 1986

[54] PACEMAKER BATTERY IMPEDANCE TEST CIRCUIT AND METHOD OF OPERATION

[75] Inventor: John G. Frost, Santa Clara, Calif.

[73] Assignee: Telectronics N.V., Curacao, Netherlands Antilles

[21] Appl. No.: 675,625

[22] Filed: Nov. 28, 1984

[51] Int. Cl.$^4$ .............................................. A61N 1/38
[52] U.S. Cl. ............................................ 128/419 PG
[58] Field of Search ................. 128/419 PG, 419 PS, 128/419 PT

[56] References Cited

U.S. PATENT DOCUMENTS 4,345,603  8/1982  Schulman ................... 128/419 PT
4,448,197  5/1984  Nappholz et al. ............ 128/419 PT Primary Examiner—William E. Kamm
Attorney, Agent, or Firm—Gottlieb, Rackman & Reisman

[57] ABSTRACT

A circuit for measuring the internal impedance of the cell of a heart pacer in order that the remaining life of the cell can be estimated. The test is performed by cutting off all current flow from the cell to the pacer circuitry, the pacer still being powered, however, by the conventional by-pass capacitor. When the cell impedance test is conducted, a test capacitor is placed across the cell and it charges exponentially with a time constant which is a function of the cell impedance. By measuring the time required for the test capacitor potential to reach a reference level, the cell impedance can be ascertained. The measured parameter can be telemetered out of the pacer along with other data in the conventional manner. With a typical lithium iodide cell, the internal impedance of the cell varies from less than 100 ohms when new, to tens of kilohms near the end of the cell life.

5 Claims, 4 Drawing Figures

PACEMAKER BATTERY IMPEDANCE TEST CIRCUIT AND METHOD OF OPERATION

DESCRIPTION

This invention relates to implantable medical devices, and more particularly to circuits for testing the internal impedance of the power source of a pacemaker or other medical device.

Ever since the first pacemaker was implanted, remaining battery life has been a parameter of primary concern. Numerous systems have been devised for determining the remaining life of battery cells. There exists a great need, however, for a system which will enable the accurate prediction of the remaining life of a pacemaker battery, while that battery continues to power the pacemaker.

The most widespread power sources for implantable pacemakers at the present time are lithium iodide and other lithium based cells. The internal impedance of such a cell can be used as an indication of its remaining life. The internal impedance (resistance) of a new cell is less than 100 ohms. The resistance increases throughout the life of the battery to tens of kilohms. Significantly, the open-circuit voltage of a lithium iodide cell remains constant throughout the cell life. In accordance with the principles of my invention, these battery characteristics are used to provide an indication of remaining battery life.

Also in accordance with the principles of my invention, I provide a test capacitor, in addition to other capacitors which may be utilized in the pacemaker. Under control of pacemaker logic provided for this purpose, the test capacitor is initially discharged. Immediately thereafter, the battery is cut off from powering the pacemaker circuitry, the conventional by-pass capacitor which is provided anyway for filtering purposes serving to power the pacemaker. The battery is now used solely to charge the test capacitor. A lithium cell, as any pacemaker battery, can be thought of as a battery and an internal resistor. The voltage across the test capacitor increases exponentially to the open-circuit battery voltage with a time constant equal to the product of the test capacitor and the internal resistance of the battery. The time required for the test capacitor to charge to a reference voltage level is a measure of the internal cell resistance, and that in turn allows the remaining cell life to be estimated. The time required for charging of the test capacitor can be transmitted to an external monitor using conventional pacemaker telemetry circuits. In this regard, reference is made to Money et al U.S. Pat. No. 4,448,196 which discloses the measurement and telemetering of voltage levels in a heart pacer.

Further objects, features and advantages of my invention will become apparent upon consideration of the following detailed description in conjunction with the drawing, in which.

Figure 1:
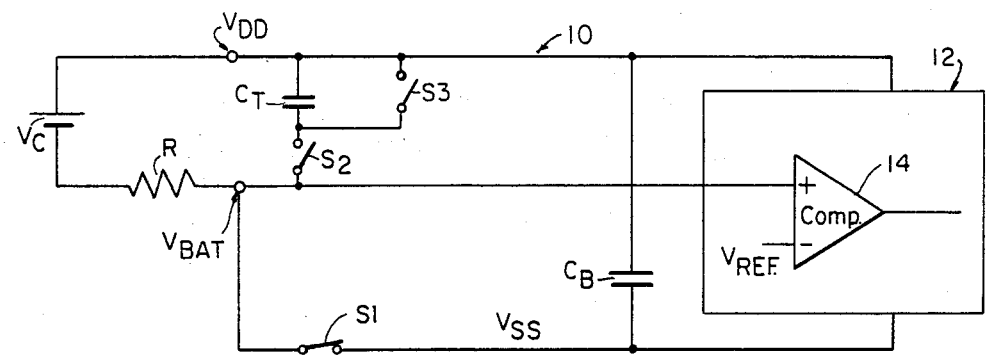
FIG. 1 depicts an illustrative embodiment of my invention, the figure being designed to illustrate the functional aspects of the invention as opposed to a detailed logic implementation.

Referring to FIG. 1, the numeral 10 represents an implantable heart pacer, with the numeral 12 representing the bulk of the pacer circuitry. The only functional element shown in FIG. 1 is comparator 14. The battery which powers the pacer is shown by its Thevenin's equivalent, a zero-resistance potential source of magnitude $V_C$ and an internal resistance of magnitude R. The battery is placed across two terminals, the potentials of which are $V_{DD}$ and $V_{BAT}$. During normal operation switch S1 is closed and a potential $V_{SS}$ appears at the right side of the switch. By-pass capacitor $C_B$ has the potential $V_{DD}$-$V_{SS}$ across it, and it is this potential which powers the pacer circuitry. Capacitor $C_B$ is a conventional component found in every implantable pacer as part of the power supply filter.

The cell impedance test of my invention requires an additional capacitor $C_T$, as well as switches S1, S2 and S3. These elements are depicted in FIG. 1. Operation of the circuit is best understood with reference to FIGS. 1 and 2 together, the latter figure depicting the potential at the $V_{BAT}$ terminal and the output of comparator 14 as a function of time.

Figure 2:
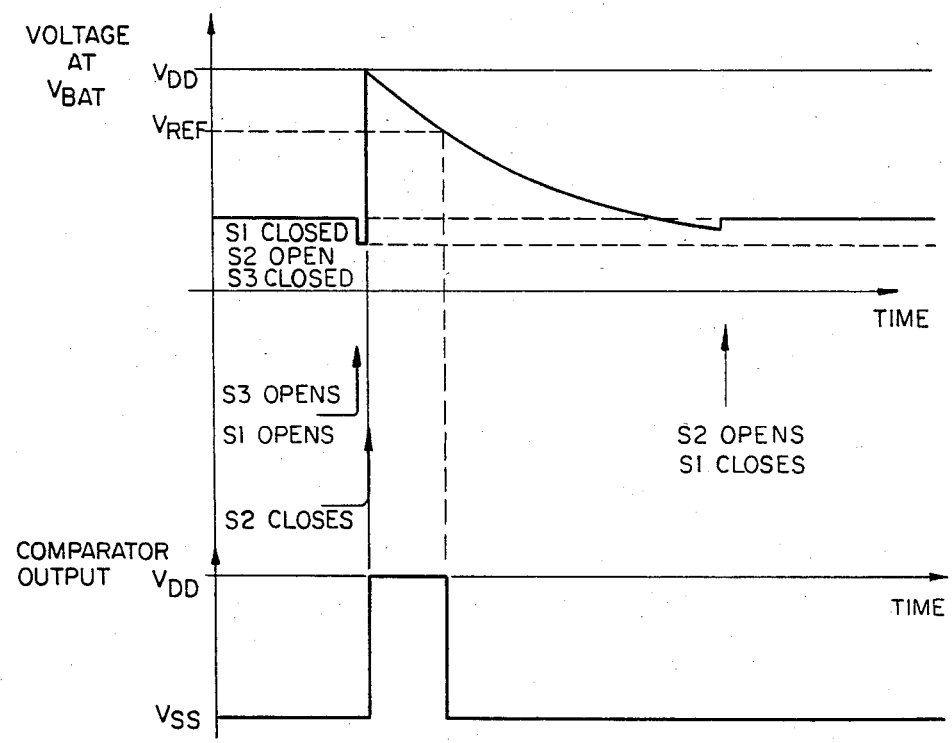
FIG. 2 depicts two waveforms as a function of time which will be helpful in analyzing the operation of the circuit of FIG. 1.

During normal operation, as indicated at the left of FIG. 2, switch S2 is open, and switches S1 and S3 are closed. With switch S2 open, capacitor $C_T$ of FIG. 1 is effectively out of the circuit. With switch S1 closed, the potential difference $V_{DD}$-$V_{SS}$ appears across by-pass capacitor $C_B$. Treating potential $V_{DD}$ as the reference, potential $V_{SS}$ is the potential supplied by the cell for powering the pacer.

Because switch S2 is normally open, it makes little difference whether switch S3 is open or closed; switch S2 prevents current flow through capacitor $C_T$ and switch S3. At the beginning of the cell impedance test, however, switch S3 is closed (even in an embodiment in which it was previously open) for a time sufficient to ensure that capacitor $C_T$ is discharged, e.g., 2 milliseconds. It is this condition which is shown at the left of FIG. 2.

Switches S3 and S1 then open, followed almost immediately by the closing of switch S2. With the opening of switch S1, the pacer is powered solely by the charge stored in capacitor $C_B$. With switch S3 open and switch S2 closed, current now flows in the clockwise direction of FIG. 1 through the cell ($V_C$ and R), capacitor $C_T$ and switch S2. Thus the discharged capacitor $C_T$ is placed across the cell with internal resistance R.

The waveform for the voltage at $V_{BAT}$ shows a momentary increase in negative potential between the opening of switches S1 and S3, and the closing of switch S2. The reason for this is that as soon as switch S1 opens and while switch S2 still remains open, no current flows through the cell and the potential $V_{BAT}$ relative to potential $V_{DD}$ is the open-circuit potential of the cell. There is no longer an IR drop across the internal resistance which tends to reduce the magnitude of the $V_{BAT}$ potential. As soon as switch S2 closes, the $V_{BAT}$ potential rises to $V_{DD}$ as shown in FIG. 2 because the potential across capacitor $C_T$ is zero (and in the idealized circuit of FIG. 1 it is assumed that the potential across switch S2 is also zero).

During normal operation, the $V_{BAT}$ potential is more negative than the $V_{REF}$ potential as shown in FIG. 2.

Since the $V_{BAT}$ potential is applied to the plus input of comparator 14, the plus input is more negative than the minus input and the comparator output is negative as indicated in FIG. 2. But as soon as the $V_{BAT}$ potential rises to $V_{DD}$, the $V_{REF}$ threshold is crossed and the comparator output goes positive since the plus input is now less negative than the minus input. The output of the comparator going high is an indication that the charging of capacitor $C_T$ has started.

As current now flows through capacitor $C_T$ and switch S2, the voltage across the capacitor increases exponentially to the open-circuit battery voltage with a time constant equal to ($RC_T$), where $C_T$ represents the magnitude of the capacitance. The $V_{BAT}$ potential as a function of time is shown in FIG. 2. When the $V_{BAT}$ potential becomes more negative than the $V_{REF}$ potential (the latter illustratively being $-0.9$ volts with respect to $V_{DD}$, a fixed potential easily derivable in a typical integrated circuit), the comparator output goes low once again. The duration of the time that the comparator output is high is a function of the cell resistance R, and it can be calculated as follows:

$$V_{BAT} = -V_C[1 - \exp(-t/RC_T)]$$

where time t is measured from the closing of switch S2. This equation can be rearranged as follows:

$$R = -t/[C_T \ln(1 + V_{BAT}/V_C)].$$

At some time $t = T$, the comparator output goes low once again when $V_{BAT} = V_{REF}$. At this time, $$R = -T/[C_T \ln(1 + V_{REF}/V_C)].$$

Typically, $V_C = 2.8$ volts and $V_{REF} = -0.9$ volts. With a test capacitor $C_T = 0.1$ uF, suppose that the comparator output goes low once again when $T = 200$ us. Substituting these values in the equation for R, $R = 5.2$ kohm.

After the comparator output has gone low, or after some predetermined time interval, switch S1 is closed once again so that the cell can power the pacer. At the same time, switch S2 is opened so that capacitor $C_T$ is out of the circuit. Switch S3 can remain open or it can be closed, as long as it is closed at the start of the next test cycle to ensure that capacitor $C_T$ is fully discharged prior to the closing of switch S2. The capacitor has to be fully discharged in order that the time interval measurement be meaningful. (As shown in FIG. 2, switch S2 opens and switch S1 closes relatively late in the test cycle—after capacitor $C_T$ has actually charged so much that the potential across it is greater than the powering potential $V_{SS}$ during normal operation; this is why there is a small drop in the magnitude of $V_{BAT}$ when normal operation resumes. Should the test cycle terminate before capacitor $C_T$ has charged to such an extent, the $V_{BAT}$ potential would indicate a drop in FIG. 2 rather than a rise.)

Figure 3:
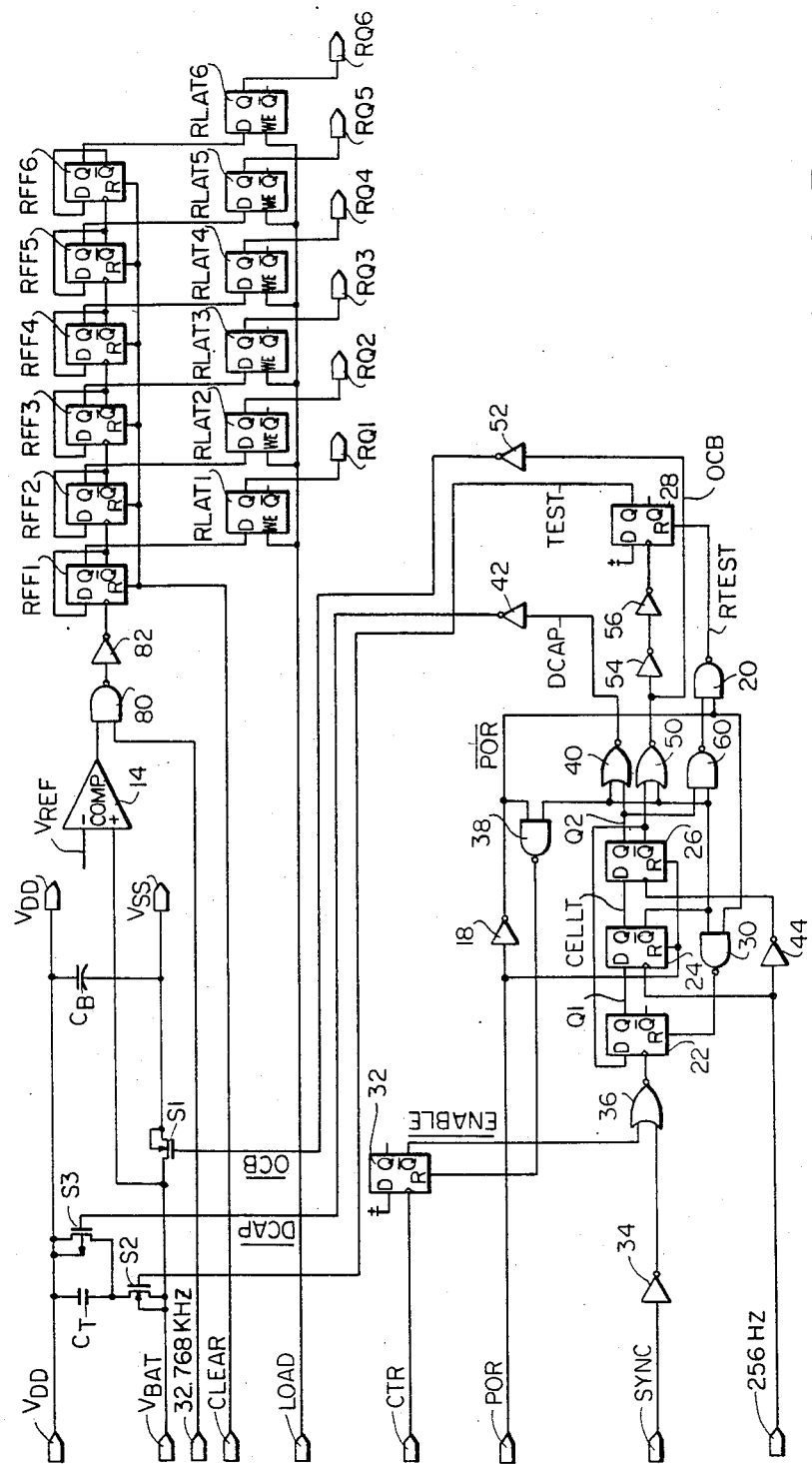
FIG. 3 depicts detailed logic circuitry for implementing the control functions in the illustrative embodiment of the invention.

The circuit of FIG. 3 is a preferred embodiment of the invention for implementing the cell impedance test. The waveforms of FIG. 4 characterize the operation of the circuit of FIG. 3. At the top left of FIG. 3, the $V_{DD}$ and $V_{BAT}$ terminals are shown, together with by-pass capacitor $C_B$ which is placed across $V_{DD}$ and $V_{SS}$. Not shown in the drawing is the actual battery which is connected on the left side between the $V_{DD}$ and $V_{BAT}$ terminals. Comparator 14 is also shown, together with the $V_{REF}$ potential applied to its minus input. Also shown in the upper left corner of FIG. 3 is the test capacitor $C_T$, the three switches S1, S2 and S3, and the $V_{SS}$ terminal. Switches S1 and S2 are N-channel MOSFET devices, while switch S3 is a P-channel MOSFET device. The logic circuit 12 of FIG. 1 also generates several other signals as indicated on the left side of FIG. 3. Two of these are conventional clock signals of 256 Hz and 32.768 KHz. The other signals generated by the logic circuit are CLEAR, LOAD, CTR, POR and SYNC.

The POR signal is a conventional power-on-reset and is used to initialize the circuit at initial power-up. As shown on FIG. 4, the POR signal is a short positive pulse which is generated once during the life of the pacer, when the cell is first connected in the circuit. (Although the other signals are shown at respective levels in FIG. 4, it is to be understood that prior to the application of power and the generation of the POR pulse, signal levels are not meaningful.) Inverter 18 on FIG. 3 inverts the POR pulse and generates the $\overline{POR}$ signal. Both of the POR and $\overline{POR}$ signals are shown in FIG. 4.

The $\overline{POR}$ pulse is applied to an input of NAND gate 20, whose RTEST output goes high during the power-on-reset initialization. Flip-flop 28 is thus reset. The $\overline{POR}$ pulse also causes the outputs of NAND gates 30 and 38 to go high to reset flip-flops 22 and 32. The POR signal resets flip-flops 24 and 26 directly.

Figure 4:
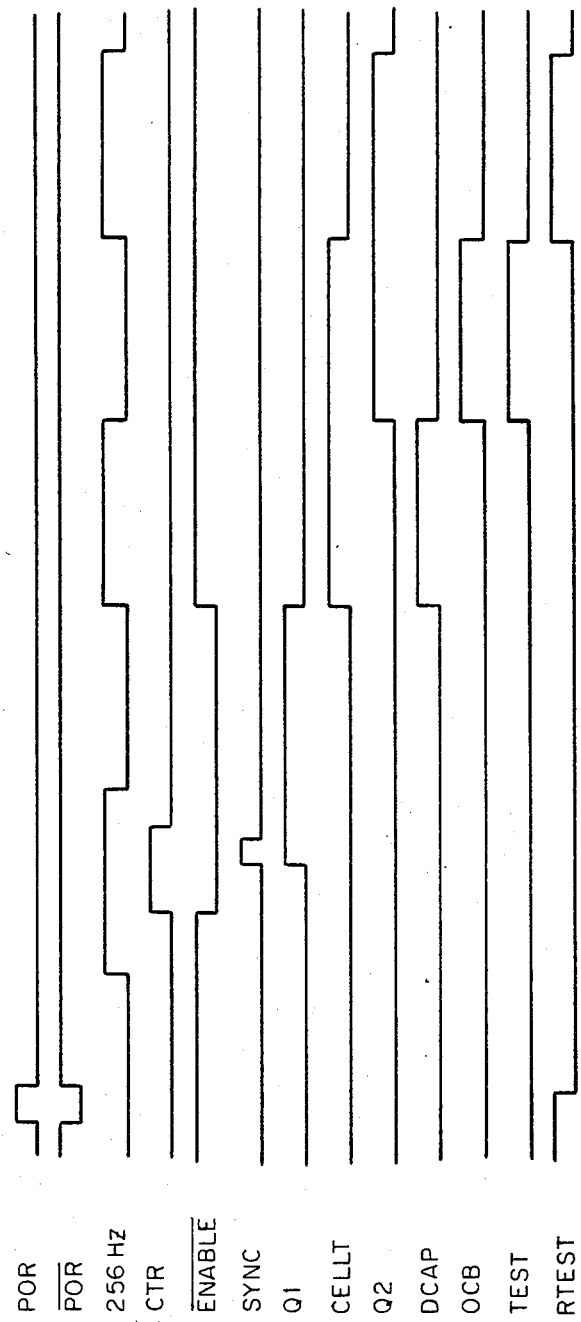
FIG. 4 is a set of waveforms which characterize operation of the logic circuit of FIG. 3.

The CTR ("cell test request") input is pulsed as shown in FIG. 4. The D input of flip-flop 32 is held high, and consequently the flip-flop is set when the CTR signal first goes high. The $\overline{Q}$ output of the flip-flop, the $\overline{ENABLE}$ line, is ordinarily high, but goes low when the flip-flop is first set as indicated in FIG. 4. The test cycle is not initiated, however, simply by the CTR line going high. An additional SYNC pulse must be generated. This positive pulse is inverted by inverter 34. With the $\overline{ENABLE}$ signal now low as well as the output of inverter 34, both inputs of NOR gate 36 are low, and the output of the gate goes high. Flip-flop 22 is thus clocked. Its D input is connected to the $\overline{Q}$ output of flip-flop 26 which is initially high. Thus flip-flop 22 is set and its Q output goes high. This output is the Q1 signal indicated in FIG. 3. As shown in FIG. 4, the Q1 signal goes high on the leading edge of the SYNC pulse; it is the setting of flip-flop 22 which initiates the test cycle. (In the illustrative embodiment of the invention, the CTR pulse is not sufficient for triggering a test cycle; the CTR pulse readies the circuit but it is actually the SYNC pulse which triggers the cycle. This dual control allows the test circuit to be synchronized to other events taking place in the pacer circuit if it is desired to do so. From the point of view of the present invention, all that is important is that some signal be generated at the start of the test cycle to control the setting of flip-flop 22.)

As indicated in FIG. 4, flip-flop 24 is then clocked on the next rising edge of the 256-Hz clock. Since its D input is connected to the Q1 line, flip-flop 24 is set. The Q output of this flip-flop goes high; this is the CELLT ("cell test") signal indicated in FIG. 4. The test cycle described above with reference to FIG. 1 actually begins with the CELLT signal going high, i.e., upon the setting of flip-flop 24. The $\overline{Q}$ output of the flip-flop goes low when the flip-flop is set, and consequently the output of NAND gate 30 goes high to reset flip-flop 22. This is shown in FIG. 4 with the Q1 signal going low on the first rising edge of the 256-Hz waveform after the CTR pulse. Similarly, NAND gate 38 now has one of its inputs low so that its output goes high to reset flip-flop 32. In FIG. 4, the $\overline{\text{ENABLE}}$ signal is shown going high at this time. The output of gate 36 is now held low so that flip-flop 22 cannot be set again until the start of another test cycle with the pulsing of the CTR input.

When flip-flop 24 is first set and its $\overline{Q}$ output goes low to reset flip-flops 22 and 32, the input of NOR gate 40 which was previously high now goes low. The other input of the gate is connected to the Q output of flip-flop 26 which is still low. Consequently, the output of gate 40 causes conductor DCAP ("discharge capacitor") to go high. The output of inverter 42 now forces the $\overline{\text{DCAP}}$ output to go low to close switch S3. This is the switch which, as shown in FIG. 1, is used to discharge test capacitor $C_T$. It is this switch which must be closed immediately prior to the opening of switch S1 in order to insure that the test capacitor is fully discharged.

At the next falling edge of the 256-Hz clock signal, the output of inverter 44 goes high to clock flip-flop 26. Since the D input of this flip-flop is connected to the CELLT line which is now high, the flip-flop is set and the Q2 line goes high as indicated in FIG. 4. When the Q2 line goes high, it causes three events to take place. First, the output of gate 40 now goes low. This is shown in FIG. 4 with the DCAP signal going low; this, in turn, causes switch S3 to open. As indicated in FIG. 2, switch S1 opens at the same time; now that capacitor $C_T$ has been discharged and switch S3 is being opened so that the charging test current can begin to flow, switch S1 must be opened so that the current which flows is determined solely by the test capacitor and the internal resistance of the battery, and is not affected by current which would otherwise be drawn by the remainder of the pacer circuitry. With the $\overline{Q}$ output of flip-flop 26 now low, both inputs of gate 50 are low and the gate output goes high. This output is connected to the OCB ("open circuit battery") line, and FIG. 4 shows the OCB signal going high. Inverter 52 inverts the signal and the negative $\overline{\text{OCB}}$ signal causes switch S1 to open.

When the output of gate 50 goes high, the positive potential is extended through inverters 54 and 56 to clock flip-flop 28. Since the D input of the flip-flop is connected to a positive potential, the Q output of the flip-flop goes high. The Q output of the flip-flop, the TEST line, is connected to the gate of switch S2 so that this switch now closes. The two inverters 54 and 56 are provided so that there is a short delay between the opening of switches S1 and S3, and the closing of switch S2, as indicated in FIG. 2. In FIG. 4, the TEST signal is shown going high together with the OCB signal going high and the DCAP signal going low. In actuality, the TEST signal is delayed slightly, as shown in exaggerated form in FIG. 2. The reason for this is that it is important for all current flow to the pacer circuitry from the cell to cease before the test current actually starts to flow. Otherwise, the $V_{BAT}$ potential and the charging of capacitor $C_T$ would be a function of the current being drawn by the pacer as well as the internal impedance of the cell. By ensuring that all current flow from the cell ceases before switch S2 closes, it is certain that the only current which charges capacitor $C_T$ is the current whose flow is determined solely by the time constant $RC_T$.

On the next rising edge of the 256-Hz clock, flip-flop 24 is clocked once again. Because the Q1 conductor is now low, the flip-flop is reset and the CELLT signal goes low as indicated in FIG. 4. As soon as the $\overline{Q}$ output of flip-flop 24 goes high once again, the output of gate 50 goes low. The OCB signal thus goes low as indicated in FIG. 4, and switch S1 closes so that normal powering of the pacer by the cell can resume. Both inputs of gate 60 are now high and the output of this gate goes low. This in turn causes the output of gate 20, the RTEST signal, to go high and to reset flip-flop 28. Thus when the RTEST signal goes high as indicated in FIG. 4, the TEST signal goes low in order that switch S2 open. As indicated in FIG. 2, switch S1 closes and switch S2 opens at the end of the test cycle. The operation of comparator 14 has nothing to do with the later opening of switch S2 and closing of switch S1.

As far as the control circuitry is concerned, all of the signals are now in their initial states except for the Q2 signal which is still high and the RTEST signal which is still high, as indicated in FIG. 4. On the next falling edge of the 256-Hz clock waveform, the output of inverter 44 goes high to clock flip-flop 26. Because the CELLT line is now low, flip-flop 26 is reset. Thus the Q2 signal goes low. Since the Q2 signal is an input of gate 60, the output of gate 60 goes high. At this time both inputs of gate 20 are high so that the RTEST signal goes low. The entire circuit is restored and another cycle can ensue with the generation of the CTR and SYNC command pulses.

As shown in FIG. 3, the $V_{BAT}$ signal and the reference voltage are applied to respective inputs of comparator 14. The 32.768 KHz clock signal is applied to one input of NAND gate 80, and the comparator output is applied to the other input. The CLEAR line is pulsed high to reset all of flip-flops RFF1–RFF6 prior to the start of the test. The output of inverter 82 goes high to energize the clock input of flip-flop RFF1 whenever the output of NAND gate 80 goes low, and the output of this gate goes low only when the 32.768 KHz clock goes high and the output of the comparator is high. Referring to FIG. 2, the output of the comparator is high only while $V_{BAT}$ exceeds $V_{REF}$. The six flip-flops are arranged as a six-stage counter, since the $\overline{Q}$ output of each stage is connected to the clock input of the succeeding stage. Consequently, the count represented by the counter is directly proportional to the time interval during which the output of comparator 14 remains high. A 32.768-KHz clock translates to a period of about 30 microseconds. With reference to FIGS. 2 and 4, the OCB signal is high, i.e., switch S1 is open, for less than 2 milliseconds. Even if the comparator output is high for only a few tenths of a millisecond, that is still several hundred microseconds so that a resolution of about 30 microseconds is adequate.

Once flip-flops RFF1–RFF6 represent a time interval (cell impedance), the stored value can be telemetered out of the pacer in order that the measured cell resistance be determined. The LOAD line can be pulsed to clock flip-flops RLAT1–RLAT6 so that the measured value can be latched. The resulting 6-bit value at terminals RQ1–RQ6 can be used by the pacer telemetry circuit for transmission to an external monitor.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

I claim:

1. A test system for ascertaining the remaining life of the battery of an implantable medical device by determining its internal impedance; said medical device including a battery, circuitry, and means for connecting said battery across said circuitry; the test system comprising test capacitor means; first switch means for disconnecting said battery from across said circuitry; second switch means for connecting said battery across said test capacitor means; means for operating both of said first and second switch means simultaneously; means for comparing the potential across said test capacitor means with a reference level; and means for measuring the time interval required for the potential across said test capacitor means to reach said reference level while said first and second switch means are operated simultaneously.

2. A test system in accordance with claim 1 further including third switch means for discharging said test capacitor means prior to the operation of said second switch means.

3. A test system in accordance with claim 1 further including by-pass capacitor means connected across said circuitry for powering said circuitry when said first switch means is operated.

4. A test method for ascertaining the remaining life of the battery of an implantable medical device by determining its internal impedance; said medical device including a battery, circuitry, means for connecting said battery across said circuitry, and a test capacitor; the method comprising the steps of disconnecting said battery from across said circuitry and simultaneously connecting said battery across said test capacitor; and determining the internal impedance of said battery by comparing the potential across said test capacitor with a reference level, and measuring the time interval required for the potential across said test capacitor to reach said reference level while said battery is disconnected from across said circuitry and is simultaneously connected across said test capacitor.

5. A test method of accordance with claim 4 further including the step of discharging said test capacitor prior to connecting said battery across said test capacitor.

* * * * *